US00PP36264P3

(12) United States Plant Patent
Espin

(10) Patent No.: US PP36,264 P3
(45) Date of Patent: Nov. 26, 2024

(54) GRAPEVINE PLANT NAMED 'Gensel 4'

(50) Latin Name: *Vitis vinifera*
Varietal Denomination: Gensel 4

(71) Applicant: Special New Fruit Licensing Mediterráneo S.L. (SNFL Mediterráneo S.L.), Murcia (ES)

(72) Inventor: Juan Carreño Espin, Murcia (ES)

(73) Assignee: Special New Fruit Licensing Mediterráneo S.L. (SNFL Mediterráneo S.L.), Murcia (ES)

( * ) Notice: Subject to any disclaimer, the term of this patent is extended or adjusted under 35 U.S.C. 154(b) by 0 days.

(21) Appl. No.: 18/078,583

(22) Filed: Dec. 9, 2022

(65) Prior Publication Data

US 2024/0196769 P1 Jun. 13, 2024

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

(56) References Cited

U.S. PATENT DOCUMENTS

| | | | |
|---|---|---|---|
| PP9,865 | P | 4/1997 | Ralli et al. |
| PP33,448 | P2 | 9/2021 | Martinez |
| PP34,722 | P2 | 11/2022 | Espin |
| PP34,723 | P2 | 11/2022 | Espin |

*Primary Examiner* — Kent L Bell
(74) *Attorney, Agent, or Firm* — Dentons US LLP

(57) ABSTRACT

'Gensel 4' is a new and distinct grapevine plant with novel characteristics that include good fertility, naturally loose bunches, and tolerance to *Erysiphe necator* and *Plasmopara viticola*, which are the main diseases of this species. The berries produced by 'Gensel 4' are red and seedless with a crisp texture and neutral flavor and no detectable seed traces. The berries produced by 'Gensel 4' are small, weighing 4.1 g/berry on average, and harvested in early July in Murcia Region (Spain).

1 Drawing Sheet

Latin name of the genus and species of the plant claimed: *Vitis vinifera.*

Cultivar denomination: 'Gensel 4'.

BACKGROUND OF THE INVENTION

The present invention relates to a new distinct variety of seedless grapevine named 'Gensel 4' having tolerance to the main diseases of its species such as *Erysiphe necator* and *Plasmopara viticola*. The new variety originated from a hybridization performed in Murcia, Spain during 2017 between '12-3-73' also known as 'ITUMFIFTEEN' (U.S. Plant Pat. No. 33,448), as the pollen parent, and 'RS12-1-230' (not patented), as the seed parent. Abortive seed traces were embryo cultured and the resulting plant was planted in an evaluation block during 2018. The first evaluation of the fruit produced by 'Gensel 4' was performed during 2019. 'Gensel 4' was first asexually propagated by field grafting dormant hardwood scions to 1103 Paulsen Rootstock (not patented) in 2020 in Murcia, Spain. Fruit from the resulting four grafted 'Gensel 4' vines was first harvested in 2021. All characteristics and distinctions remain true to form and are established and transmitted through succeeding propagations.

SUMMARY OF THE INVENTION

The following are the most outstanding and distinguishing characteristics of 'Gensel 4'. 'Gensel 4' produces naturally small (4.1 g/berry) seedless red berries (5 R3/4) with tolerance to *Erysiphe necator* and *Plasmopara viticola*. The berries produced by 'Gensel 4' have a broad ellipsoid shape with an excellent neutral sweet flavour and crisp texture, that are harvested in early July in Murcia-Spain.

'Gensel 4' is believed to be most similar to 'Ralli Seedless' (U.S. Plant Pat. No. 9,865). Nonetheless, the new cultivar can be distinguished from 'Ralli Seedless' based at least upon harvest period, fertility, cluster and berry size. 'Gensel 4' matures in early July whereas 'Ralli Seedless' matures in mid-July in Murcia-Spain (15 days after). 'Gensel 4' has a fertility index of 1.3 while 'Ralli Seedless' has 0.6 fertility index. The bunches produced by 'Gensel 4' are less heavy (400 g) than the bunches produced by 'Ralli Seedless' (500-750 g). 'Gensel 4' produces berries smaller (4.1 g) than the berries of 'Ralli Seedless' (average 4.1 g v. 6 g).

'Gensel 4' can be distinguished from its male parent, '12-3-73', in that the new cultivar is harvested in early July whilst the harvest time of '12-3-73' is in mid-July (15 days later) in Murcia, Spain. 'Gensel 4' clusters are less heavy than '12-3-73' clusters (average 400 g v. 600 g). The berries of 'Gensel 4' have a broad ellipsoidal shape whereas the berries of '12-3-73' have a globose shape. The berries of '12-3-73' have muscat flavour whilst the berries of 'Gensel 4' have a neutral flavour.

'Gensel 4' can be distinguished from its female parent, 'RS12-1-230', in that the berries of 'Gensel 4' are red whereas the berries of 'RS12-1-230' are white. The berries of 'Gensel 4' are seedless whilst the berries of 'RS12-1-230' are seeded.

BRIEF DESCRIPTION OF THE DRAWING

FIG. 1—Shows the form, foliage, and fruit of a 2-year-old 'Gensel 4' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'Gensel 4'. The detailed description was obtained between March and November using 2-year-old plants grown in the field in Murcia, Spain. The color references are to the *Munsell Plant Tissue Color Book,* 2012 Edition by Munsell Color.

Classification:
- *Family*.—Vitaceae.
- *Botanical.—Vitis vinifera.*
- *Common name*.—Grapevine.
- *Cultivar name*.—'Gensel 4'.

Plant:
- *Plant habit and growth*.—Erect.
- *Age at maturity*.—2 years old.
- *Size* (*at maturity*).—Height: 225 cm. Width: 300 cm.
- *Vigor*.—Low.
- *Productivity*.—High, 1.3 fertility index, around 50 pounds/plant and 10 Tn/acre.
- *Rootstock*.—Name of rootstock: 1103 Paulsen Rootstock (not patented). Age of rootstock at time of grafting: one year old.

Trunk:
- *Size*.—Diameter: 4 cm. Height (at measured diameter of 4 cm): 45 cm above the ground.
- *Shape*.—Straight and cylindrical.
- *Surface texture*.—Rough, straight grained with the outer layer easily removed.
- *Bark color*.—Exterior 5YR5/2. Interior 5YR4/2.

Canes:
- *Size*.—Diameter: 8.7 mm. Length: 180 cm.
- *Surface texture*.—Mature cane: smooth, glabrous. Inmature cane: very smooth, very finely ribbed, glabrous.
- *Form* (*woody shoot cross section form*).—Circular; pith in center with diaphragm at nodes.
- *Color*.—Mature: 5 months, 5GY5/6 (anthocyanins: 2.5R5/4). Immature: 4 weeks, 5GY4/8. Dorsal side of internodes: 5GY6/6; anthocyanins: 2.5R5/4. Ventral side of internodes: 5GY6/6. Dorsal side of nodes: 5GY6/6; anthocyanins: 2.5R5/4. Ventral side of nodes: 5GY6/6; anthocyanins: 2.5R5/4.
- *Internode length* (*upper mature sun cane*).—16.2 cm.
- *Internode width* (*upper mature sun cane*).—7.90 mm.
- *Node width*.—14.50 mm.

Bud:
- *Bud description*.—Winter bud: rounded, pointed, color 5YR4/4. Green bud: rounded and pointed, color 5GY6/6.
- *Time of bud burst*.—16 February.
- *Time of bud leaf burst*.—24 February.

Tendrils:
- *Form*.—Mostly trifid, curly.
- *Size*.—Medium.
- *Length*.—24 mm.
- *Diameter*.—2.50 mm.
- *Texture and distribution of tendril at each node beginning at base*.—Very smooth, discontinuous, 0000000010000010010101 0 (0 means no tendril at that node and 1 means there is tendril at the node).
- *Color*.—Mature: 4 weeks, 2.5GY7/8. Inmature: 10 days, 2.5GY6/10.
- *Anthocynanin*.—Mature: absent. Immature: absent.

Growing tips (young shoot):
- *Pubescence*.—Absent.
- *Color*.—5GY5/6.
- *Anthocynanin*.—Absent.
- *Shape*.—Fully open.
- *Apex*.—Triangular.
- *Form of tip*.—Fully open.
- *Shoot attitude before tying*.—Erect.

Leaves:
- *Shape*.—Wedge-shaped.
- *Apex*.—Pointed.
- *Base*.—Cuneiform.
- *Number of lobes*.—5.
- *Arrangement*.—The leaves are arranged in alternative and opposite pattern. A phyllotaxy ½ pattern.
- *Depth of upper lateral sinuses of mature leaves*.—Medium.
- *Arrangement of lobes of upper lateral sinuses on mature leaves*.—Slightly overlapped.
- *Margin*.—Irregular teeth.
- *Length of teeth on margin*.—2 to 12 mm.
- *Shape of teeth on margin*.—Both sides convex.
- *Texture* (*mature leaf*).—Upper surface: smooth, flat, without blistering or goffering, glabrous. Lower surface: smooth, very low density of prostrate hairs between the main veins on the lower side of the blade.
- *Size*.—Immature: Length: 10 days, 6.25 cm. Width: 10 days, 6 cm. Mature: Length: 4 weeks, 21.5 cm. Width: 4 weeks, 18 cm. Ratio of length/width of teeth (mature leaf): small.
- *Color*.—Immature leaf: Upper surface: 5GY5/6, anthocyanins 5Y5/6. Lower surface: 5GY5/6. Mature leaf: Upper surface: 5GY4/6. Lower surface: 5GY5/4. Autumn coloration: Upper surface: 2.5Y8/8. Lower surface: 2.5Y8/6.
- *Venation*.—Pattern: palmate (veins on upper leaf are flat; veins on lower leaf are raised), without anthocyanins coloration. Length of middle vein in mature leaves: 17.3 cm. Color: Upper surface: 2.5GY7/6. Lower surface: 2.5GY7/4.
- *Petiolar sinus*.—Open, brace-shaped.
- *Petiole*.—Length: 11.6 cm. Diameter: 3.25 mm. Color: 2.5GY7/6, anthocyanins 2.5R5/6.

Floral cluster:
- *General description and location*.—Mostly in the $2^{nd}$ and $4^{th}$ node, 80% with shoulders.
- *Quantity of inflorescences per cluster*.—351.
- *Size*.—Length: 18.8 cm. Width: 6.2 cm hanging; 10 cm with shoulders spread.
- *Peduncle*.—Length: 5.5 cm. Diameter: 2.32 mm. Color: 2.5GY6/8.
- *Inflorescences*.—Hermaphroditic.
- *Stamens*.—5 per flower, straight, 2.2 mm.
- *Anthers*.—Small, nondescript.

*Pistil*.—Bottle-shaped whose ovary is septate and contains 4 ovules.

*Date of bloom*.—Start: 22 April, 50%: 25 April, 100%: 29 April.

*Pollen amount*.—Sparse.

*Pollen color*.—5GY8/10.

*Calyptra*.—5 segments, complete separation.

*Calyptra color*.—5GY5/8.

*Flower height*.—2 mm.

*Flower diameter*.—1.9 mm.

*Petal(s)*.—Number of petals: 5 petals. Arrangement: the petals are fused together as a cap at the tip (calyptra). Shape: a cap with 5 fused petals. Length: 2.6 mm. Width: 1.4 mm. Apex: fused petals, as a cap. Margin descriptors: smooth. Texture (Upper Surface): smooth. Texture (Lower Surface): smooth. Color (Upper Surface): 5GY5/8. Color (Lower Surface): 5GY5/10.

*Calyx*.—Very reduced, dome-shaped, and formed by 5 sepals join together. Size: very small (non-measured). Texture: smooth. Color (Upper Surface): 5GY6/8.

Fruit:

*Time of year of commercial harvest and shipment*.—Very early season, July 8, in Murcia, Spain.

*Time of beginning of berry ripening*.—Very early, Jun. 26, 2023, in Murcia, Spain.

*Keeping quality*.—After 30 days of cold storage the variety keeps the color, but the rachis shows poor conditions as the primary and secondary stem are dehydrated. Some berries crumble.

*Cluster* (*primary bunches*).—Generally size: medium (380 g tipped and 400 g not tipped). Length (without peduncle): 21.7 cm tipped and 27 cm not tipped. Width: 12.3 cm hanging, 22 cm with shoulders spread. Density: low. Peduncle length: 8.5 cm. Peduncle diameter: 5.4 mm. Peduncle color: 2.5GY 6/6. Number of berries per cluster: 118 tipped and 133 not tipped (on average). Berry: Size: small (4.1 g). Diameter: 18.12 mm. Length: 19.33 mm. Shape: broad ellipsoid. Uniformity: very uniform. Brix content: 22.8° Brix. Titratable acidity: 0.5. Skin color (without bloom): 5R3/4. Skin color (with bloom): 5R3/6. Pedicel: Length: 7.3 mm. Diameter: 1.17 mm. Color: 5GY7/6. Strength of attachment to berry: strong, 15%.

*Cluster* (*secondary bunches*).—Generally size: small, 135.7 g. Length (without peduncle): 10.5 cm. Width: 9.7 cm hanging; 15.7 cm with shoulders spread. Density: low. Peduncle length: 6.7 cm. Peduncle diameter: 3.6 mm. Peduncle color: 2.5GY7/8. Number of berries per cluster: 45 (on average). Berry: Size: small, 3 g. Diameter: 16.1 mm. Length: 18 mm. Shape: broad ellipsoid. Uniformity: very uniform. Brix content: 19.8° Brix. Titratable acidity: 0.54. Skin color (without bloom): 5R3/4. Skin color (with bloom): 5R3/6. Pedicel: Length: 6.7 mm. Diameter: 0.9 mm. Color: 2.5GY7/6. Strength of attachment to berry: strong, 15%.

Berry flesh:

*Color*.—2.5GY8/4.

*Juice, color*.—5Y8/6.

*Juice production*.—High, 54%.

*Thickness of skin*.—Thick.

*Flavor*.—Neutral.

*Fragrance*.—Neutral.

*Texture*.—Crisp, 79 shores.

*Seeds*.—Seed rudiments, non-detectable.

*Use*.—Table grape.

Disease and insect resistance: This cultivar is tolerant to the main diseases of this species such as *Erysiphe necator* and *Plasmopara viticola*. This cultivar is susceptible to diseases and insects of its species, such as *Botrytis cinerea, Daktulosphaira vitifoliae, Ceratitis capitata, Planococcus ficus, Planococcus citri, Empoasca vitis*.

What is claimed is:

1. A new and distinct variety of grapevine plant named 'Gensel 4' as shown and described herein.

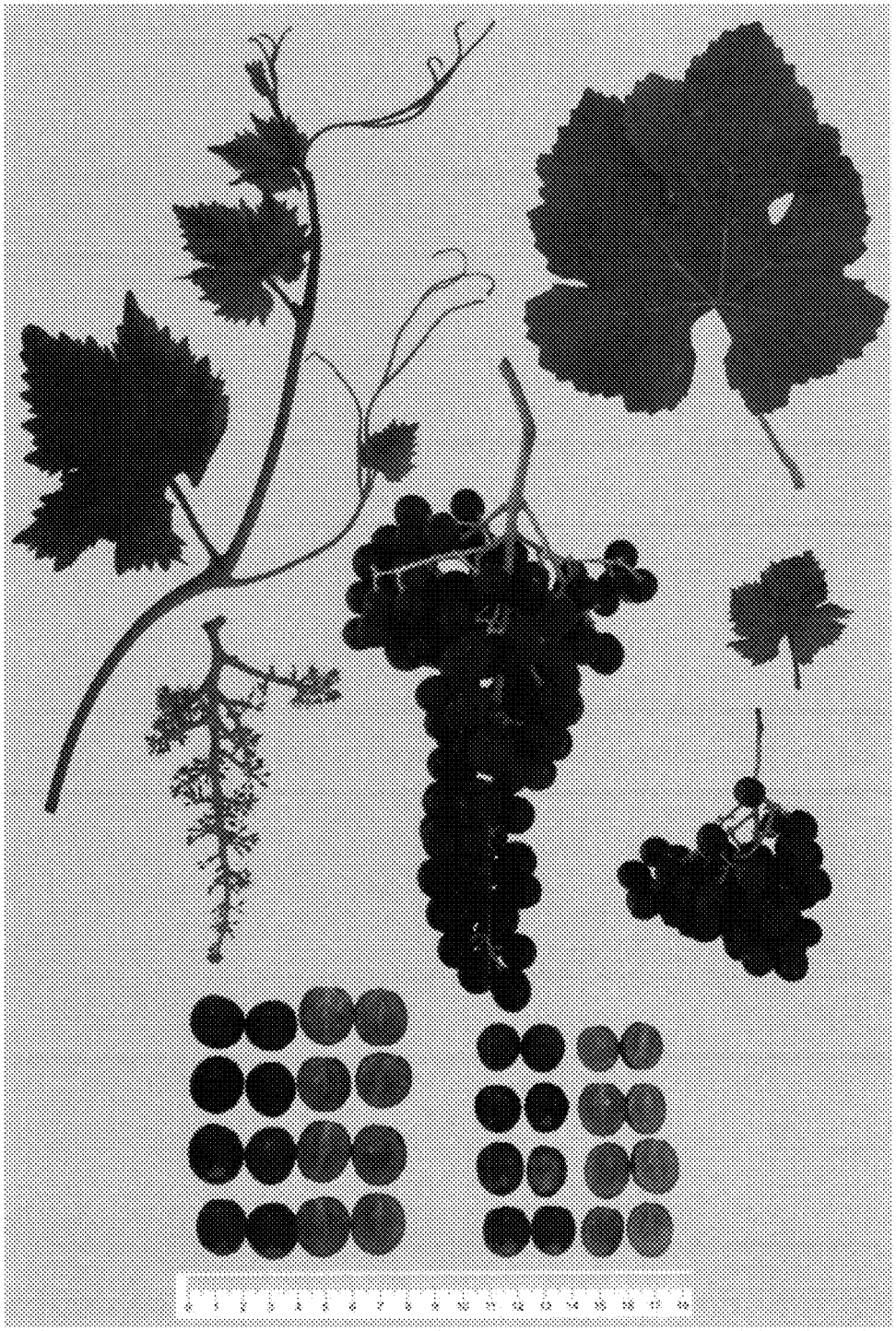

* * * * *